US00PP36375P2

(12) United States Plant Patent
Koot

(10) Patent No.: US PP36,375 P2
(45) Date of Patent: Jan. 7, 2025

(54) ***PETUNIA* PLANT NAMED 'Dopetpotplucor 24'**

(50) Latin Name: ***Petunia* X *hybrida***
Varietal Denomination: Dopetpotplucor 24

(71) Applicant: DUMMEN GROUP B.V., De Lier (NL)

(72) Inventor: Arjan Koot, Oeffelt (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/384,868

(22) Filed: Oct. 29, 2023

(51) Int. Cl.
*A01H 5/02* (2018.01)
*A01H 6/82* (2018.01)

(52) U.S. Cl.
USPC ..... Plt./356.23
CPC ..... *A01H 6/824* (2018.05)

(58) Field of Classification Search
USPC ..... Plt./356.23
CPC ..... A01H 5/02
See application file for complete search history.

(56) References Cited

PUBLICATIONS https://www.flickr.com/photos/193742037@N08/52796729873/in/photostream/; Apr. 5, 2023; 1 page.*
https://www.youtube.com/watch?v=5fLG1rPBm3l; Mar. 30, 2023; 1 page.*
https://www.facebook.com/DummenOrangeNA/videos/2454561218057982; Apr. 25, 2023; 1 page.*
https://na.dummenorange.com/app/pdfcatalogs/detail.web?catalogId=225; Feb. 20, 2024; 6 pages.*
https://www.facebook.com/photo/?fbid=674009814734766&set=pcb.674010148068066; Apr. 20, 2023; 1 page.*

* cited by examiner

*Primary Examiner* — Kent L Bell
(74) *Attorney, Agent, or Firm* — C. Anne Whealy

(57) ABSTRACT

A new and distinct cultivar of *Petunia* plant named 'Dopetpotplucor 24', characterized by its compact and uniformly mounding plant habit; moderately vigorous growth habit and moderate growth rate; freely branching habit; early and freely flowering habit; large soft red-colored flowers; and good container and garden performance.

2 Drawing Sheets

Figure 1:
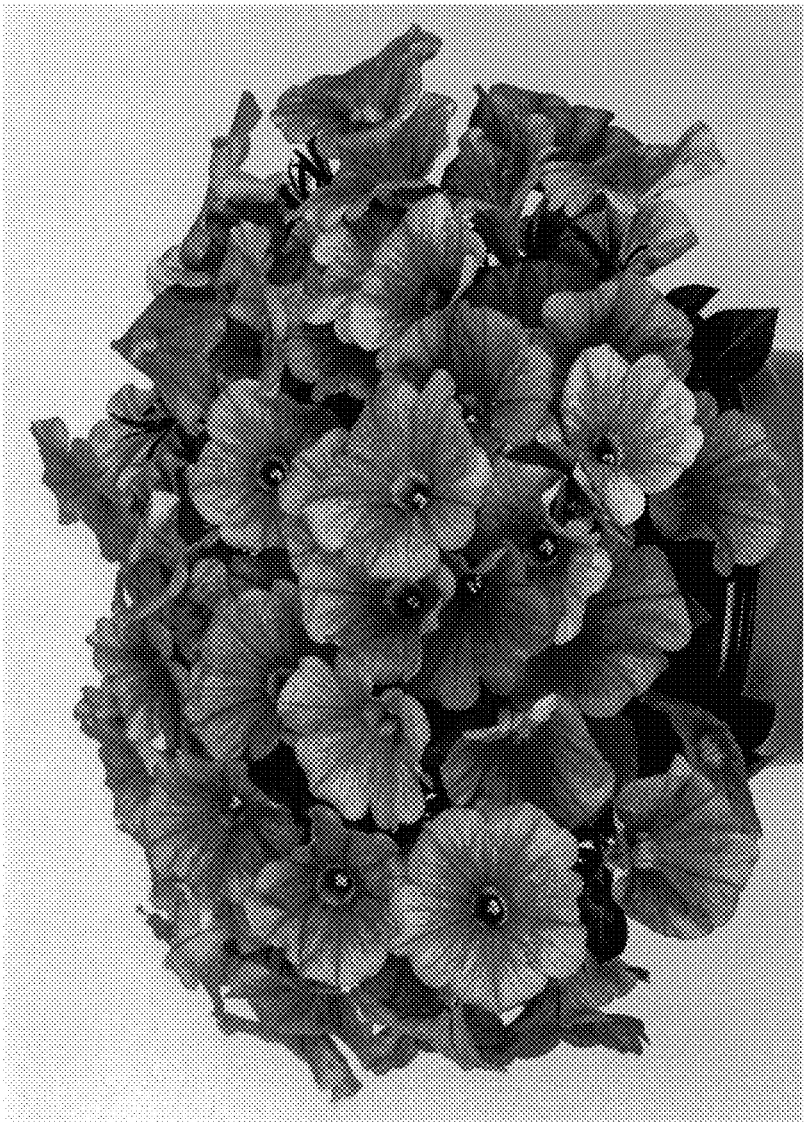

Botanical designation: *Petunia* X *hybrida.*
Cultivar denomination: 'DOPETPOTPLUCOR 24'.

BACKGROUND OF THE INVENTION

The present invention relates to a new and distinct cultivar of *Petunia* plant, botanically known as *Petunia* X *hybrida* and hereinafter referred to by the name 'Dopetpotplucor 24'.

The new *Petunia* plant is a product of a planned breeding program conducted by the Inventor in Rheinberg, Germany. The objective of the breeding program is to create new compact, freely branching and early-flowering *Petunia* plants with numerous attractive flowers.

The new *Petunia* plant originated from a cross-pollination made by the Inventor in July 2020 in Rheinberg, Germany of a proprietary selection of *Petunia* X *hybrida* identified as code number TT20-K0286, not patented, as the female, or seed, parent with a proprietary selection of *Petunia* X *hybrida* identified as code number TT20-K0851, not patented, as the male, or pollen, parent. The new *Petunia* plant was discovered and selected by the Inventor as a single flowering plant from within the progeny of the stated cross-pollination in a controlled greenhouse environment in Rheinberg, Germany in May 2021.

Asexual reproduction of the new *Petunia* plant by terminal vegetative cuttings in a controlled greenhouse environment in Rheinberg, Germany since May 2021 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopetpotplucor 24'. These characteristics in combination distinguish 'Dopetpotplucor 24' as a new and distinct *Petunia* plant:

1. Compact and uniformly mounding plant habit.
2. Moderately vigorous growth habit and moderate growth rate.
3. Freely branching habit.
4. Early and freely flowering habit.
5. Large soft red-colored flowers.
6. Good container and garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are more freely flowering than plants of the female parent selection.
2. Flowers of plants of the new *Petunia* are soft red in color whereas flowers of plants of the female parent selection are purple in color.

3. Flowers of plants of the new *Petunia* resist fading whereas flowers of plants of the female parent selection fade with development.

Plants of the new *Petunia* can be compared to plants of the male parent selection. In side-by-side comparisons, plants of the new *Petunia* differ primarily from plants of the male parent selection in the following characteristics:

1. Plants of the new *Petunia* are more freely flowering than plants of the male parent selection.
2. Flowers of plants of the new *Petunia* are soft red in color whereas flowers of plants of the male parent selection are soft pink in color.
3. Flowers of plants of the new *Petunia* resist fading better than flowers of plants of the male parent selection.

Plants of the new *Petunia* can be compared to plants of *Petunia* X *hybrida* 'Sunremi', disclosed in U.S. Plant Pat. No. 16,803. In side-by-side comparisons, plants of the new *Petunia* and 'Sunremi' differ primarily in the following characteristics:

1. Plants of the new *Petunia* are more compact than and not as vigorous as plants of 'Sunremi'.
2. Plants of the new *Petunia* are more freely branching than plants of 'Sunremi'.
3. Plants of the new *Petunia* flower earlier than plants of 'Sunremi'.
4. Flowers of plants of the new *Petunia* are soft red in color whereas flowers of plants of 'Sunremi' are darker red in color.
5. Plants of the new *Petunia* are resistant to Tobacco Mosaic Virus whereas plants of 'Sunremi' are not resistant to Tobacco Mosaic Virus.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet FIG. 1 is a side perspective view of a typical flowering plant of 'Dopetpotplucor 24' grown in a container.

Figure 2:
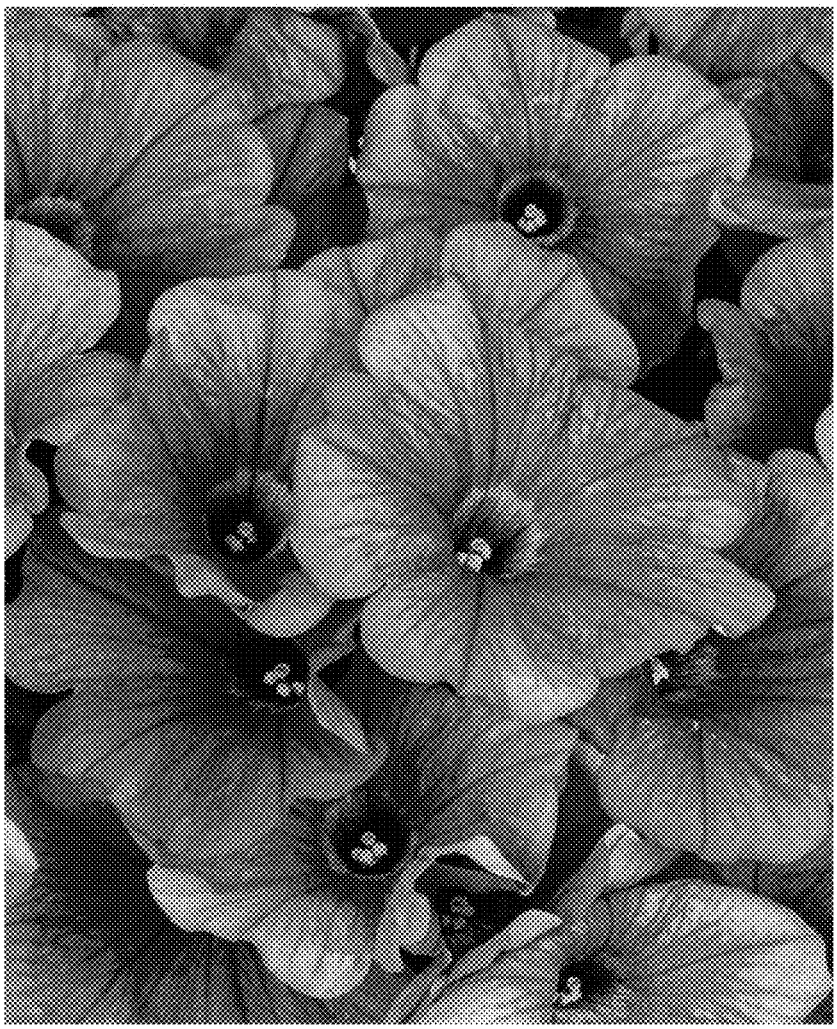

The photograph on the second sheet FIG. 2 is a close-up view of typical flowers of 'Dopetpotplucor 24'.

DETAILED BOTANICAL DESCRIPTION

The aforementioned photographs and following observations, measurements and values describe plants grown during the spring and summer in 22-cm containers in a glass-covered greenhouse in Rheinberg, Germany and under cultural practices typical of commercial *Petunia* production. During the production of the plants, day and night temperatures averaged 18 C and light levels averaged 4,500 lux. Plants were twelve weeks old when the photographs were taken and 25 weeks old when the description was taken. In the following description, color references are made to The Royal Horticultural Society Colour Chart, Fifth Edition, except where general terms of ordinary dictionary significance are used.

Botanical classification: *Petunia* X *hybrida* 'Dopetpotplucor 24'.

Parentage:

*Female, or seed, parent*.—Proprietary selection of *Petunia* X *hybrida* identified as code number TT20-K0286, not patented.

*Male, or pollen, parent*.—Proprietary selection of *Petunia* X *hybrida* identified as code number TT20-K0851, not patented.

Propagation:

*Type*.—By terminal vegetative cuttings.

*Time to initiate roots, summer*.—About five days at temperatures about 20 C.

*Time to initiate roots, winter*.—About seven days at temperatures about 20 C.

*Time to produce a rooted young plant, summer*.—About three weeks at temperatures about 20 C.

*Time to produce a rooted young plant, winter*.—About four weeks at temperatures about 20 C.

*Root description*.—Fine, fibrous; close to 155B in color, actual color of the roots is dependent on substrate composition, water quality, fertilizers, substrate temperature and age of roots.

*Rooting habit*.—Freely branching; dense.

Plant description:

*Plant and growth habit*.—Compact and uniformly mounding plant habit; freely branching habit with about three to four primary lateral branches each with about ten secondary branches developing after pinching; moderately vigorous growth habit and moderate growth rate.

*Plant height, soil level to top of foliar plane*.—About 13 cm.

*Plant height, soil level to top of floral plane*.—About 19 cm.

*Plant diameter*.—About 70 cm.

Lateral branch description:

*Length*.—About 36 cm.

*Diameter*.—About 4.5 mm.

*Internode length*.—About 1 cm.

*Strength*.—Moderately strong.

*Aspect*.—Initially upright to somewhat outwardly spreading.

*Texture and luster*.—Pubescent; semi-glossy.

*Color, developing*.—Close to 146B.

*Color, developed*.—Close to 144A.

Leaf description:

*Arrangement*.—Before flowering, alternate; after flowering, opposite; simple.

*Length*.—About 3.9 cm.

*Width*.—About 1.9 cm.

*Shape*.—Spatulate.

*Apex*.—Obtuse.

*Base*.—Attenuate.

*Margin*.—Entire.

*Texture and luster, upper and lower surfaces*.—Pubescent; coriaceous; semi-glossy.

*Venation pattern*.—Pinnate; arcuate.

*Color*.—Developing leaves, upper surface: Close to 137B. Developing leaves, lower surface: Close to 146B. Fully expanded leaves, upper surface: Close to 147A; venation, close to 144C. Fully expanded leaves, lower surface: Close to 147B; venation, close to 144B.

*Petioles*.—Length: About 5.5 mm. Diameter: About 3 mm. Strength: Moderately strong; firm. Texture and luster, upper and lower surfaces: Smooth, glabrous; matte. Color, upper and lower surfaces: Close to 138A.

Flower description:

*Flower type and flowering habit*.—Single salverform flowers arising from leaf axils; freely flowering habit with usually about 265 flowers and flower buds developing per plant during the flowering season; flowers face mostly upright to outwardly.

*Fragrance*.—None detected.

*Natural flowering season*.—Plants flower continuously during the spring and summer in Germany; early flowering habit, plants typically beginning flowering about nine weeks after planting.

*Flower longevity*.—Individual flowers last about two to three days on the plant; flowers persistent.

*Flower buds*.—Length: About 4.4 cm. Diameter: About 9 mm. Shape: Ovoid. Texture and luster: Rippled; semi-glossy. Color: Close to 75B.

*Flower diameter*.—About 5.9 cm by 6 cm.

*Flower depth* (*height*).—About 5.5 cm.

*Flower throat diameter*.—About 1.1 cm.

*Flower tube length*.—About 2.8 cm.

*Flower tube diameter, proximally*.—About 7.5 mm.

*Corolla*.—Arrangement: Five petals fused at the base and opening into a flared trumpet. Petal lobe length (from throat): About 2.9 cm. Petal lobe width: About 3.2 cm. Petal shape: Roughly spatulate. Petal apex: Obtuse, rounded. Petal margin: Entire; slightly undulate. Petal texture and luster, upper and lower surfaces: Rippled, glabrous; semi-glossy. Throat texture and luster: Rippled; semi-glossy. Tube texture and luster: Rippled; semi-glossy. Color: Petal lobe, when opening, upper surface: Close to 50A. Petal lobe, when opening, lower surface: Close to 55C. Petal lobe, fully opened, upper surface: Close to 51A; venation, close to 46A and N137A; color becoming closer to 55B with subsequent development. Petal lobe, fully opened, lower surface: Close to 55C; venation, close to 144A; color becoming closer to 55D with subsequent development. Flower throat: Close to 166B; venation, close to 183B. Flower tube: Close to 161A; venation, close to 144B.

*Sepals*.—Arrangement: Five sepals fused at the base forming a tubular star-shaped calyx. Length: About 1.4 cm. Diameter: About 2 mm. Shape: Oblong. Apex: Rounded. Base: Decurrent. Margin: Entire. Texture and luster, upper and lower surfaces: Smooth, glabrous; semi-glossy. Color: When opening and fully opened, upper surface: Close to N137A. When opening and fully opened, lower surface: Close to 138A.

*Peduncles*.—Length: About 2.3 cm. Diameter: About 1.5 mm. Strength: Moderately strong. Texture and luster: Smooth, glabrous; semi-glossy. Color: Close to 144A.

*Reproductive organs*.—Stamens: Quantity per flower: Five. Filament length: About 1.4 cm. Filament color: Close to 157A. Anther length: About 2 mm. Anther shape: Ovate. Anther color: Close to 162D. Pollen amount: Abundant. Pollen color: Close to 160B. Pistils: Quantity per flower: One. Pistil length: About 2.6 cm. Style length: About 1.8 cm. Style color: Close to 145B. Stigma diameter: About 2 mm. Stigma shape: Rounded. Stigma color: Close to 145D. Ovary color: Close to 137A and 138B. Fruits: Quantity produced per plant: About 180 during the flowering season. Length: About 7 mm. Diameter: About 3 mm. Texture: Smooth, glabrous. Color: Close to 199A. Seeds: Quantity per flower: About 220. Length: About 0.2 mm. Diameter: About 0.2 mm. Texture: Smooth, glabrous. Color: Close to 202A.

Garden performance: Plants of the new *Petunia* have been observed to have good garden performance and tolerate wind, rain, temperatures ranging from about 5 C to about 40 C and to be hardy to USDA Hardiness Zone 11.

Pathogen & pest resistance: Plants of the new *Petunia* have been observed to be resistant to Tobacco Mosaic Virus. To date, plants of the new *Petunia* have not been observed to be resistant to pests and other pathogens common to *Petunia* plants.

It is claimed:

1. A new and distinct *Petunia* plant named 'Dopetpotplucor 24' as illustrated and described.

* * * * *